United States Patent
Yamamoto

(10) Patent No.: US 10,365,251 B2
(45) Date of Patent: Jul. 30, 2019

(54) APPARATUS WITH LASER CONTROLLING UNIT WHICH DECREASES A TIME DIFFERENCE BETWEEN SUBSEQUENTLY PULSED LASERS

(71) Applicant: CANON KABUSHIKI KAISHA, Tokyo (JP)

(72) Inventor: Hiroshi Yamamoto, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 282 days.

(21) Appl. No.: 15/185,127

(22) Filed: Jun. 17, 2016

(65) Prior Publication Data

US 2017/0005450 A1    Jan. 5, 2017

(30) Foreign Application Priority Data

Jun. 30, 2015  (JP) ................................ 2015-131223

(51) Int. Cl.
*H01S 3/094* (2006.01)
*H01S 3/00* (2006.01)
(Continued)

(52) U.S. Cl.
CPC ....... *G01N 29/2418* (2013.01); *A61B 5/0095* (2013.01); *H01S 3/094076* (2013.01); *H01S 3/0014* (2013.01); *H01S 3/0092* (2013.01); *H01S 3/092* (2013.01); *H01S 3/1022* (2013.01); *H01S 3/115* (2013.01); *H01S 3/1625* (2013.01); *H01S 3/1636* (2013.01); *H01S 3/1643* (2013.01); *H01S 3/23* (2013.01)

(58) Field of Classification Search
CPC .............. G01N 29/2418; A61B 5/0095; H01S 3/094076; H01S 3/23; H01S 3/1625; H01S 3/1636; H01S 3/1643; H01S 3/115; H01S 3/1022; H01S 3/0014; H01S 3/0092
USPC .......................................................... 73/645
See application file for complete search history.

(56) References Cited

U.S. PATENT DOCUMENTS 4,977,565 A * 12/1990 Shimosaka ........... H01S 5/4025
                                                        372/28
6,188,469 B1 * 2/2001 Liou ......................... G01P 3/68
                                                        356/28
(Continued)

FOREIGN PATENT DOCUMENTS

CN        102000912      *   6/2014
JP        2011-014685        1/2011
(Continued)

*Primary Examiner* — Jacques M Saint Surin
(74) *Attorney, Agent, or Firm* — Venable LLP

(57) ABSTRACT

Provided is an apparatus for acquiring object information, the apparatus including: first and second laser output unit outputting first and second pulsed laser; a laser controlling unit configured to control each laser output unit; a first or second detecting unit configured to detect an emission timing of laser and output a first or second detection signal; a probe configured to receive an acoustic wave from an object being irradiated with the laser; and a signal processing unit configured to acquire specific information of the object, based on the acoustic wave. The laser controlling unit controls output of at least one of the laser output units so as to decrease a time difference between subsequent first and second pulsed lasers to be output.

16 Claims, 13 Drawing Sheets

(51) Int. Cl.
*G01N 29/24* (2006.01)
*A61B 5/00* (2006.01)
H01S 3/23 (2006.01)
H01S 3/16 (2006.01)
H01S 3/092 (2006.01)
H01S 3/115 (2006.01)
H01S 3/102 (2006.01)

(56) References Cited

U.S. PATENT DOCUMENTS

| | | | |
|---|---|---|---|
| 9,074,991 B2 | 7/2015 | Suzuki | G01N 21/1702 |
| 2004/0120050 A1* | 6/2004 | Tsukihara | B23K 26/0604 |
| | | | 359/629 |
| 2006/0166469 A1* | 7/2006 | Nakayama | H01L 21/2026 |
| | | | 438/487 |
| 2011/0182306 A1* | 7/2011 | Hosseini | H01S 3/235 |
| | | | 372/25 |
| 2012/0061356 A1* | 3/2012 | Fukumitsu | B23K 26/0613 |
| | | | 219/121.61 |
| 2014/0064030 A1 | 3/2014 | Yamamoto et al. | 367/87 |
| 2015/0374239 A1 | 12/2015 | Yamamoto et al. | |
| | | | A61B 5/0095 |

FOREIGN PATENT DOCUMENTS

| | | |
|---|---|---|
| JP | 2011-229660 | 11/2011 |
| JP | 2013-106822 | 6/2013 |

* cited by examiner

APPARATUS WITH LASER CONTROLLING UNIT WHICH DECREASES A TIME DIFFERENCE BETWEEN SUBSEQUENTLY PULSED LASERS

BACKGROUND OF THE INVENTION

Field of the Invention

The present invention relates to an apparatus with laser controlling unit which decreases a time difference between subsequently pulsed lasers.

Description of the Related Art

Photoacoustic tomography (PAT) using ultrasonic waves is a method for determining optical characteristic values, such as the absorption coefficient, in an object (e.g. living body). If a pulsed light generated from a light source is irradiated to a living body, the light propagates in the living body while being diffused. A light absorber inside the living body absorbs the propagated light and generates a photoacoustic wave (typically an ultrasonic wave). By receiving this photoacoustic wave using a probe and analyzing the received signal, an initial sound pressure distribution caused by the light absorber inside the living body can be acquired.

In PAT, the initial sound pressure P of the ultrasonic wave, which is generated in the light absorber inside the living body by light absorption, is given by the following Expression (1).

$$P = \Gamma \cdot \mu a \cdot \Phi \qquad (1)$$

Here $\Gamma$ denotes a Grueneisen coefficient which is an elasticity characteristic value, and is determined by dividing the product of a volume expansion coefficient $\beta$ and a square of the sound velocity c by specific heat $C_p$. $\mu a$ denotes an absorption coefficient of the light absorber. $\Phi$ denotes a luminous flux absorbed by the light absorber.

To accurately determine the absorption coefficient, the initial sound pressure must be sufficiently high with respect to the noise, as shown in Expression (1). For this, the quantity of light that reaches the light absorber must be increased.

One way of increasing the quantity of light that reaches the light absorber is to simultaneously irradiate a plurality of pulsed lasers to the object. In this case, if the emission timings of the plurality of pulsed lasers do not match, the pulse width of the pulsed light that reaches the light absorber becomes long. The photoacoustic wave generated in the light absorber is determined by convolution-integrating of the photoacoustic wave, which is generated when the impulse light is irradiated, with the light pulse waveform. Therefore if the pulse width is long, the time width of the photoacoustic signal becomes long as well. If the time width of the photoacoustic signal becomes long, resolution may deteriorate when the object information is generated based on the photoacoustic signal received by the probe.

In order to decrease the pulse width when pulsed lights from a plurality of pulsed lasers are combined, Japanese Patent Application Laid-Open No. 2011-229660 discloses an example of controlling the timings of the excitation start signals which instruct the start of excitation of a plurality of pulsed lasers.

Patent Literature 1: Japanese Patent Application Laid-Open No. 2011-229660

SUMMARY OF THE INVENTION

As described above, in order to maximize the effects of the photoacoustic measurement using the plurality of pulsed lasers, it is preferable to improve the resolution of object information by improving the accuracy of the emission timing control of the plurality of pulsed lasers, and to improve the resolution of the object information.

With the foregoing in view, it is an object of the present invention to minimize the pulse width when the lights of a plurality of pulsed lasers are combined in the photoacoustic measurement.

The present invention provides an apparatus, comprising:
a first and a second laser output unit configured to output a first and a second pulsed laser respectively;
a laser controlling unit configured to control the first and the second laser output unit;
a first detecting unit configured to detect an emission timing of the first pulsed laser and output a first detection signal; and
a second detecting unit configured to detect an emission timing of the second pulsed laser and output a second detection signal, wherein
the laser controlling unit controls output of at least one of the first and the second laser output unit, based on a time difference between the first and the second detection signals.

The present invention also provides an apparatus, comprising:
a first and a second laser output unit configured to output a first and a second pulsed laser respectively;
a laser controlling unit configured to control the first and the second laser output unit;
a first detecting unit configured to detect an emission timing of the first pulsed laser and output a first detection signal; and
a second detecting unit configured to detect an emission timing of the second pulsed laser and output a second detection signal, wherein
the laser controlling unit controls input energy to at least one of the first and the second laser output unit, based on a time difference between the first and the second detection signal.

The present invention also provides an apparatus, comprising:
a first and a second laser output unit configured to output a first and a second pulsed laser respectively;
a laser controlling unit configured to control the first and the second laser output unit;
a first detecting unit configured to detect an emission timing of the first pulsed laser and output a first detection signal; and
a second detecting unit configured to detect an emission timing of the second pulsed laser and output a second detection signal, wherein
the laser controlling unit controls a temperature of a laser medium of at least one of the first and the second pulsed laser, based on a time difference between the first and the second detection signal.

According to the present invention, the pulse width, when the lights of a plurality of pulsed lasers are combined, can be minimized in the photoacoustic measurement.

Further features of the present invention will become apparent from the following description of exemplary embodiments with reference to the attached drawings.

DESCRIPTION OF THE EMBODIMENTS

Figure 1A:
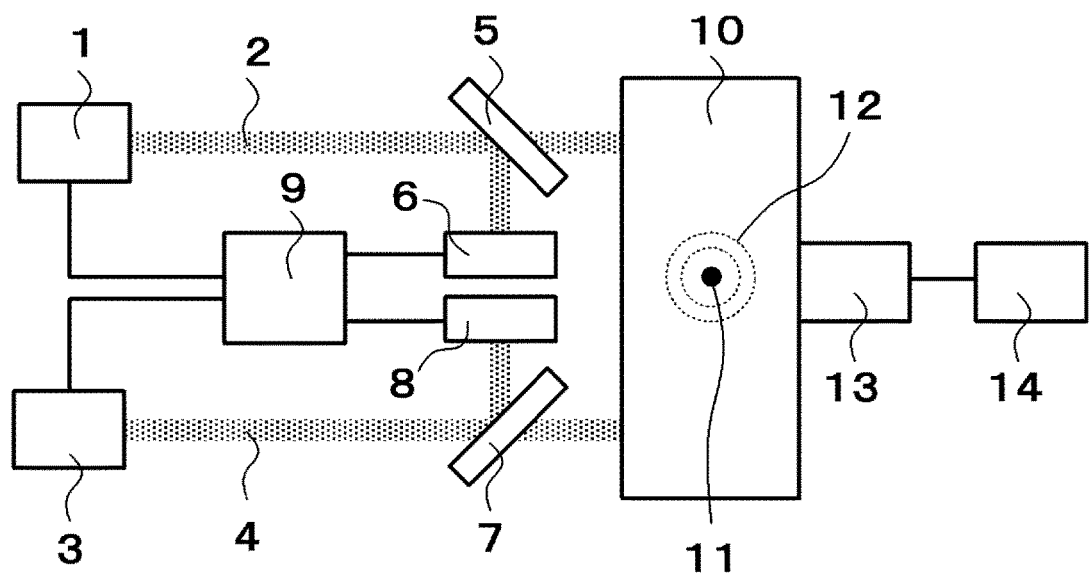
FIG. 1A is a block diagram depicting the entire apparatus of Example 1.

Preferred embodiments of the present invention will now be described with reference to the drawings. Dimensions, materials, shapes, positional relationships and the like of the components described herein below should be appropriately changed depending on the configuration and various conditions of the apparatus to which the invention is applied, and are not intended to limit the scope of the invention to the following description.

The present invention relates to a laser apparatus for generating laser light, such as a pulsed laser. The present invention can also be interpreted as a control apparatus and a control method of this laser apparatus, or as an object information acquiring apparatus that uses this laser apparatus as a light source.

If the present invention is interpreted as an object information acquiring apparatus, the present invention relates to a technique to detect an acoustic wave propagated from an object, and generate and acquire specific information on the interior of the object. Therefore the present invention can be interpreted as an object information acquiring apparatus, a control method thereof, an object information acquiring method, and a signal processing method. The present invention can also be interpreted as a program which allows an information processing apparatus, including such hardware resources as a CPU and memory, to execute these methods, or as a storage medium storing the program.

The object information acquiring apparatus of the present invention includes an apparatus based on the photoacoustic effect, and this apparatus receives an acoustic wave generated inside an object by irradiating light (electromagnetic waves) to the object, and acquires specific information on the interior of the object as the image data. Such an apparatus can also be called a "photoacoustic apparatus", a "photoacoustic tomography apparatus", a photoacoustic imaging apparatus" or the like.

This specific information is characteristic value information corresponding to each of a plurality of positions inside the object, and is generated using reception signals that are acquired by receiving the photoacoustic waves.

The specific information acquired by the present invention is a value reflecting the absorptivity of the light energy. For example, the specific information includes a generation source of the acoustic wave generated by light irradiation, initial sound pressure inside the object, light energy absorption density and absorption coefficient which are derived from the initial sound pressure, and concentration of a substance constituting the tissue. By determining oxyhemoglobin concentration and deoxyhemoglobin concentration as the substance concentration, oxygen saturation distribution can be calculated. Further, glucose concentration, collagen concentration, melanin concentration, and volume percentage of fat or water can also be determined.

Further, based on the specific information at each position inside the object, two-dimensional or three-dimensional specific information distribution can be acquired. The distribution data can be generated as image data.

An acoustic wave that is referred to in the present invention is typically an ultrasonic wave, including an elastic wave, that is called a "sound wave" and "acoustic wave". An electric signal converted from an acoustic wave by a probe or the like is also called an "acoustic signal". In the present description however, use of the term "ultrasonic wave" or "acoustic wave" is not intended to limit the wavelength of such an elastic wave. An acoustic wave generated by the photoacoustic effect is called a "photoacoustic wave" or a "light-induced ultrasonic wave". An electric signal that originates from a photoacoustic wave is also called a "photoacoustic signal".

The measurement targets of the object information acquiring apparatus of the present invention can be, for example, a living body (e.g. human body, animal body), a sample other than a living body, and a calibration sample (e.g. phantom). If the object is a living body, the present invention can be used for diagnosis of a vascular disease, follow-up examination of chemotherapy and the like.

In the case of the above mentioned apparatus disclosed in Japanese Patent Application Laid-Open No. 2011-229660, the emission timings of a plurality of pulsed lasers cannot be controlled with a resolution that exceeds the clock intervals. Normally the clock frequency used for control of a pulsed laser is about 50 MHz, and the time resolution to control the emission timings of the pulsed laser is about 20 ns. The pulse width demanded for a laser for a standard photoacoustic apparatus is about 100 ns or less. However, in order to image fine blood vessels of about a 0.03 mm level, a 20 ns or less pulse width is demanded. Therefore for high resolution photoacoustic apparatuses, a YAG (yttrium aluminum garnet) laser and a titanium sapphire (Ti:sa) laser, of which pulse widths are about 10 ns, are frequently used.

In the case of using a plurality of such laser apparatuses to acquire high output, it may be difficult to accurately match the emission timings of a plurality of pulsed lasers if the clock interval is about 20 ns, depending on the shift amount of the emission timings of the plurality of pulsed lasers. As a result, the pulse width becomes long when the lights of the plurality of pulsed lasers are combined. If the pulse width becomes long, resolution of the photoacoustic image drops. The emission timings of the plurality of pulsed lasers could be accurately matched if the clock frequency is increased, but this requires a control mechanism having a high performance crystal oscillator, which increases cost.

Example 1

(General Configuration)

An entire system configuration will now be described with reference to FIG. 1A. A reference numeral 1 denotes a first pulsed laser apparatus, and a reference numeral 2 denotes a first light. A reference numeral 3 denotes a second pulsed laser apparatus, and a reference numeral 4 denotes a second light. A reference numeral 5 denotes a first light branching unit, and a reference numeral 6 denotes a first detecting unit. A reference numeral 7 denotes a second light branching unit, and a reference numeral 8 denotes a second detecting unit. A reference numeral 9 denotes a laser controlling unit, a reference numeral 13 denotes a probe, and a reference numeral 14 denotes a signal processing unit. By this apparatus, a photoacoustic wave 12 generated from a light absorber 11 inside an object 10 is measured.

(Photoacoustic Apparatus)

As a basic hardware configuration, the photoacoustic apparatus has a plurality of (two in Example 1) pulsed laser apparatuses (1, 3), a light branching units (5, 7), detecting units (6, 8), a laser controlling unit (9), a probe (13) and a signal processing unit (14). Pulsed lights emitted from the plurality of pulsed laser apparatuses are branched by the light branching units, and a part of the lights are guided to the light detecting units respectively. The light detected by each light detecting unit is transmitted to the laser controlling unit as a detector signal. The first pulsed laser apparatus corresponds to the first laser output unit of the present invention, and the second laser apparatus corresponds to the second pulsed laser output unit of the present invention. The first detector signal corresponds to the first detection signal of the present invention, and the second detector signal corresponds to the second detection signal of the present invention.

The remaining lights are irradiated to the object. Light irradiated to the object diffuses and propagates inside the object. When a part of the energy of the propagated light is absorbed by a light absorber (which becomes a sound source), such as blood, a photoacoustic wave (typically an ultrasonic wave) is generated by the thermal expansion of the light absorber. The photoacoustic wave generated inside the object propagates through the object, and is received by the probe. The photoacoustic wave received by the probe is transmitted to the signal processing unit. The signal processing unit generates information on the interior of the object based on the transmitted photoacoustic signal.

The laser controlling unit which received the detector signals from the light detecting units calculates the time difference of the detector signals based on the emission timings of the plurality of pulsed lasers. Then the laser controlling unit controls the outputs of the plurality of pulsed laser apparatuses so that the calculated time difference becomes a predetermined value. To control the outputs, a method of controlling the energy that is input to the laser apparatus and a method of controlling the temperature of the laser apparatus can be used. In other words, if the temperature is controlled so that the gain of the laser increases, the emission timing is advanced forward, and if the temperature is controlled so that the gain of the laser decreases, the emission timing delays. The energy control and the temperature control may be combined to control the emission timings.

For example, the gain of an alexandrite crystal, which is used as the laser medium of an alexandrite laser, changes considerably depending on the temperature. In concrete terms, the gain is higher if the crystal is heated to about 80° C., rather than using the crystal at normal temperature. If the gain is higher, the time required from turning the Q switch ON to the emission of the pulsed light decreases. Using this characteristic, the pulse emission timing of the alexandrite laser can be adjusted. To adjust the temperature of the crystal, a method of adjusting the temperature of water in which the crystal is submerged, or a method of controlling the temperature of a heater attached to the crystal, can be used, for example.

(Pulsed Laser Apparatus)

In the case when the object is a living body, a pulsed light having a wavelength that is absorbed by a specific component, out of the components constituting the living body, is irradiated from the light source. In the present invention, it is preferable to use a light having a wavelength to propagate into the object. In concrete terms, this wavelength is 600 nm or more, 1100 nm or less, if the object is a living body. To acquire a high resolution photoacoustic image, it is preferable that the pulse width is about 10 nanoseconds or less. For the light source, a laser that can implement high power is preferable. However, a light emitting diode, a flash lamp or the like may be used. For the laser, various lasers can be used, such as a solid-state laser, a gas laser, a dye laser and a semiconductor laser.

(Laser Controlling Unit)

The laser controlling unit controls the timing, waveform, intensity, temperature and the like of the irradiation of the pulsed laser. If a plurality of pulsed laser apparatuses are used, the laser controlling unit may be individually disposed, or one laser controlling unit may control the plurality of pulsed laser apparatuses. The laser controlling unit may be integrated with the pulsed laser apparatus. The laser controlling unit may be disposed separately from the photoacoustic apparatus of the present invention. The laser controlling unit may be constituted by a CPU or the like.

(Light Branching Unit)

The light branching unit branches an emitted laser light, guides one side of the branched laser light to the detecting unit and the other side to the object. For the light branching unit, a glass plate can be used. A dielectric film may be formed on the surface of the glass plate, so that the reflectance of the light has a desired value. An optical member for branching the light, such as a beam splitter and half mirror, can also be used.

(Object and Light Absorber)

The object and light absorber are not a part of the photoacoustic apparatus of the present invention, but will nonetheless be described in this section. The photoacoustic apparatus of the present invention using the photoacoustic effect is intended for such purposes as imaging blood vessels, diagnosis malignant tumors and vascular diseases of humans and animals, and follow-up examination of chemotherapy. The light absorber inside the object has a relative high absorption coefficient in the object, although this depends on the wavelength of the light to be used. In concrete terms, the light absorber is water, fat, protein, oxyhemoglobin and deoxyhemoglobin or the like.

(Probe)

The probe receives a photoacoustic wave generated on the surface or the inside of a living body, and converts the photoacoustic wave into an electric signal. Any probe may be used as long as a photoacoustic signal can be received, such as a probe using piezoelectric phenomena, a probe using the resonance of light, and a probe using changes in electrostatic capacitance.

To acquire a high resolution photoacoustic image with less noise, or to decrease the measurement time, it is preferable to array a plurality of probes two-dimensionally or three-dimensionally. Further, it is preferable to dispose a scanning mechanism constituted by an XY stage, a guide, a motor apparatus or the like to scan the probe, in terms of measuring the object in different directions, or decreasing the shadow region. Further, it is preferable to contact the holding unit and the object via liquid (e.g. water) or gel in order to efficiently receive the photoacoustic wave from the object by the probe. Furthermore, a reflection film, such as a metal film, may be formed on the surface of the probe in order to return the light reflected on the surface of the object or holding unit, and the light scattered inside the object that emerges from of the object.

If the object is a breast, the breast may be held between two plate-type holding members. In this case, it is preferable to scan the probe along the surfaces of the plate. If the testee lies down on their stomach, the breast which hangs down may be held by a cup or plate-shaped holding member. In this case, a hemispherical or spherical crown-shaped support on which a plurality of probes are installed may be vertically disposed below the holding member, in which this support scans the breast of the testee on a plane parallel with the bed of the testee.

(Signal Processing Unit)

The signal processing unit generates data related to the optical characteristic value distribution information, such as the absorption coefficient distribution inside the object, using the signals received by the probe. To calculate the absorption coefficient distribution inside the object, the initial sound pressure distribution inside the object is normally calculated based on the signals received by the probe, and the absorption coefficient distribution is calculated considering the fluence of light inside the object. To generate the initial sound pressure distribution, various known methods can be used, such as back projection using time domains.

It is preferable that the signal processing unit includes processing circuits to perform amplification processing, digital conversion processing and various correction processing operations and the like for the analog electric signals output from the probe. Further, the signal processing unit includes an information processing apparatus (e.g. PC, workstation), a processor that performs information processing according to programs, and a memory that stores data and programs, and is constituted by a communication device and a display device.

The information processing apparatus constituting the signal processing unit may function as a controlling unit of a laser apparatus, or a system controlling unit such as a processing apparatus of the light detection data. In this case, each controlling unit may be constructed as a processing module that operates in the processor of the information processing apparatus.

(Configuration of Pulsed Laser Apparatus)

Figure 1B:
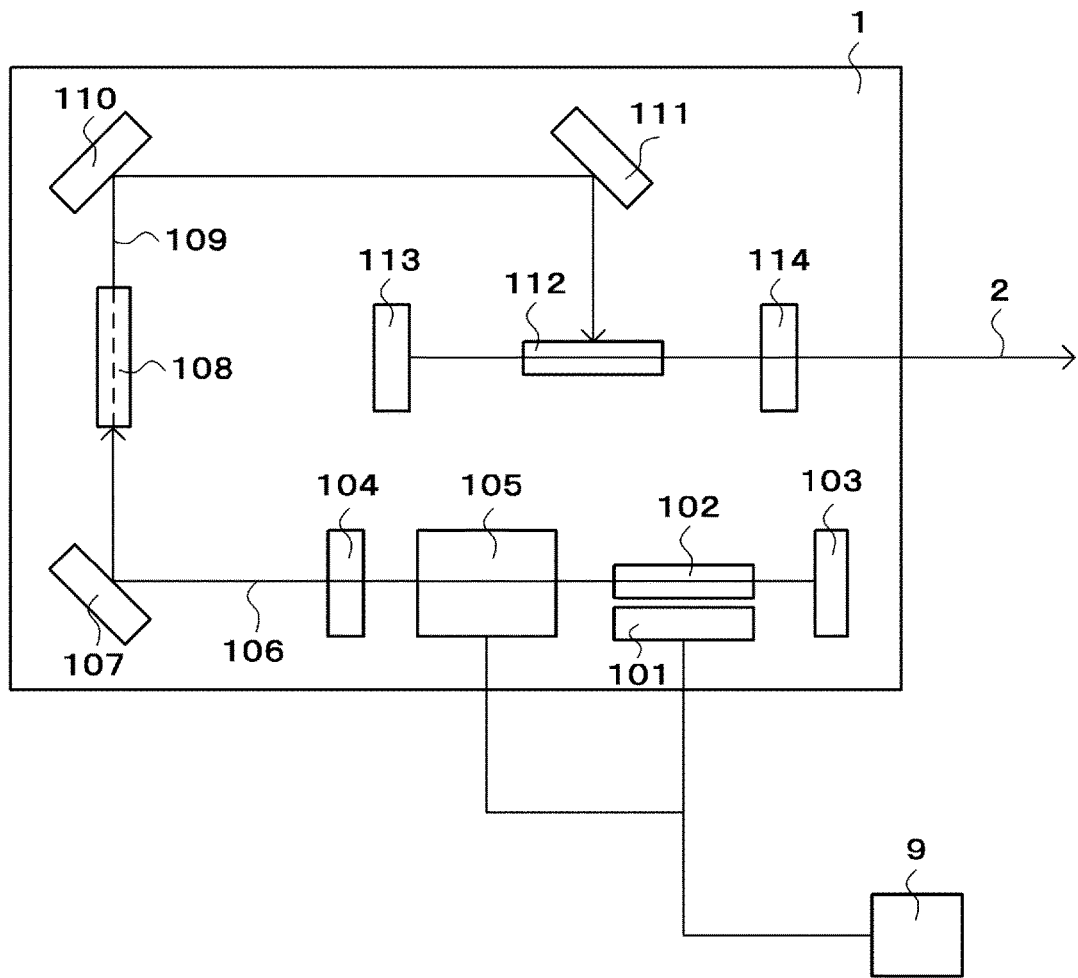
FIG. 1B is a block diagram depicting a laser apparatus of Example 1.

FIG. 1B is a diagram depicting a first pulsed laser apparatus 1. The first pulsed laser apparatus 1 and the second pulsed laser apparatus 3 are titanium sapphire lasers. A reference numeral 101 denotes a flash lamp, a reference numeral 102 denotes a YAG crystal, a reference numeral 103 denotes a YAG rear mirror, a reference numeral 104 denotes a YAG output coupler, a reference numeral 105 denotes a Q switch, and a reference numeral 106 denotes a YAG light. A reference numeral 107 denotes a first mirror, a reference numeral 108 denotes a second harmonic generation (SHG) crystal, a reference numeral 109 denotes an SHG light, a reference numeral 110 denotes a second mirror, and a reference numeral 111 denotes a third mirror. A reference numeral 112 denotes a titanium sapphire crystal, a reference numeral 113 denotes a titanium sapphire rear mirror, and a reference numeral 114 denotes a titanium sapphire output coupler. The configuration of the first pulsed laser apparatus 1, however, is not limited to this configuration. For the configuration of the second pulsed laser apparatus 3, a same configuration as the first pulsed laser apparatus 1 may be used.

The flash lamp 101 emits light by the laser controlling unit 9 applying voltage. The emitted light is absorbed by the YAG crystal 102. The YAG crystal 102, the YAG rear mirror 103, and the YAG output coupler 104 constitute a resonator. The Q switch 105 is constituted by an electro-optic crystal. If the laser controlling unit 9 applies energy, the YAG light 106, of which wavelength is 1064 nm, is emitted from the YAG rear mirror 103. The emitted YAG light enters the SHG crystal 108 via the first mirror 107.

The SHG crystal 108 converts the entered YAG light 106 into SHG light 109 of which wavelength is 532 nm, and emits the SHG light 109. The SHG light 109 enters the titanium sapphire crystal 112 via the second mirror 110 and the third mirror 111.

The titanium sapphire crystal 112, the titanium sapphire rear mirror 113, and the titanium sapphire output coupler 114 constitute a resonator. In this example, the resonator is constituted so that the wavelength of the second light 2, which is emitted from the titanium sapphire output coupler 114, becomes 757 nm. The output of the titanium sapphire laser is 120 mJ, the frequency thereof is 20 Hz, and the pulse width is 13 ns (full width at half maximum).

The first light 2 emitted from the first pulsed laser apparatus 1 is partially reflected by the first light branching unit 5, and is guided to the first detecting unit 6, as shown in FIG. 1A. In the same manner, the second light 4 emitted from the second pulsed laser apparatus 3 is partially reflected by the second light branching unit 7, and is guided to the second detecting unit 8. The lights transmitted through the first branching unit 5 and the second branching unit 7 are irradiated to the object 10. Here a phantom simulating a living body is used as the object 10. In the object 10, a $\phi$ 0.03 mm light absorber 11 is disposed.

The light diffused inside the object 10 is absorbed by the light absorber 11. Then the photoacoustic wave 12 is generated from the light absorber 11 by the photoacoustic effect, and the photoacoustic wave 12 propagates through the object 10, and is received by the probe 13. Here it is assumed that the probe 13 is a capacitive micro-machined ultrasonic transducer (CMUT). A band of the probe 13 has a 4 MHz central frequency, and a 4 MHz full width at half maximum. As a matching material for acoustic matching, water is disposed between the object 10 and the probe 13.

The signal processing unit 14 generates an initial sound pressure distribution inside the object 10 from the signals received by the probe 13. The first detector signal detected by the first detecting unit 6 and the second detector signal detected by the second detecting unit 8 are transmitted to the laser controlling unit 9. The laser controlling unit 9 calculates the time difference between the first detector signal and the second detector signal. Then the laser controlling unit 9 changes the energy to be input to each of the flash lamps of the first pulsed laser apparatus 1 and the second pulsed laser apparatus 3, so that the calculated time difference approaches 0.

(Energy Control)

A relationship between the energy to be input to the flash lamps of the first pulsed laser apparatus 1 and the second pulsed laser apparatus 3, and the emission timings thereof will be described with reference to FIG. 1C. The abscissa of the graph indicates energy [J] to be input to the flash lamp. The left axis indicates the output [mJ] of the pulsed laser. The right axis indicates the Q switch delay [ns]. The Q switch delay means the time from turning the Q switch ON to the emission of the pulsed light.

Figure 1C:
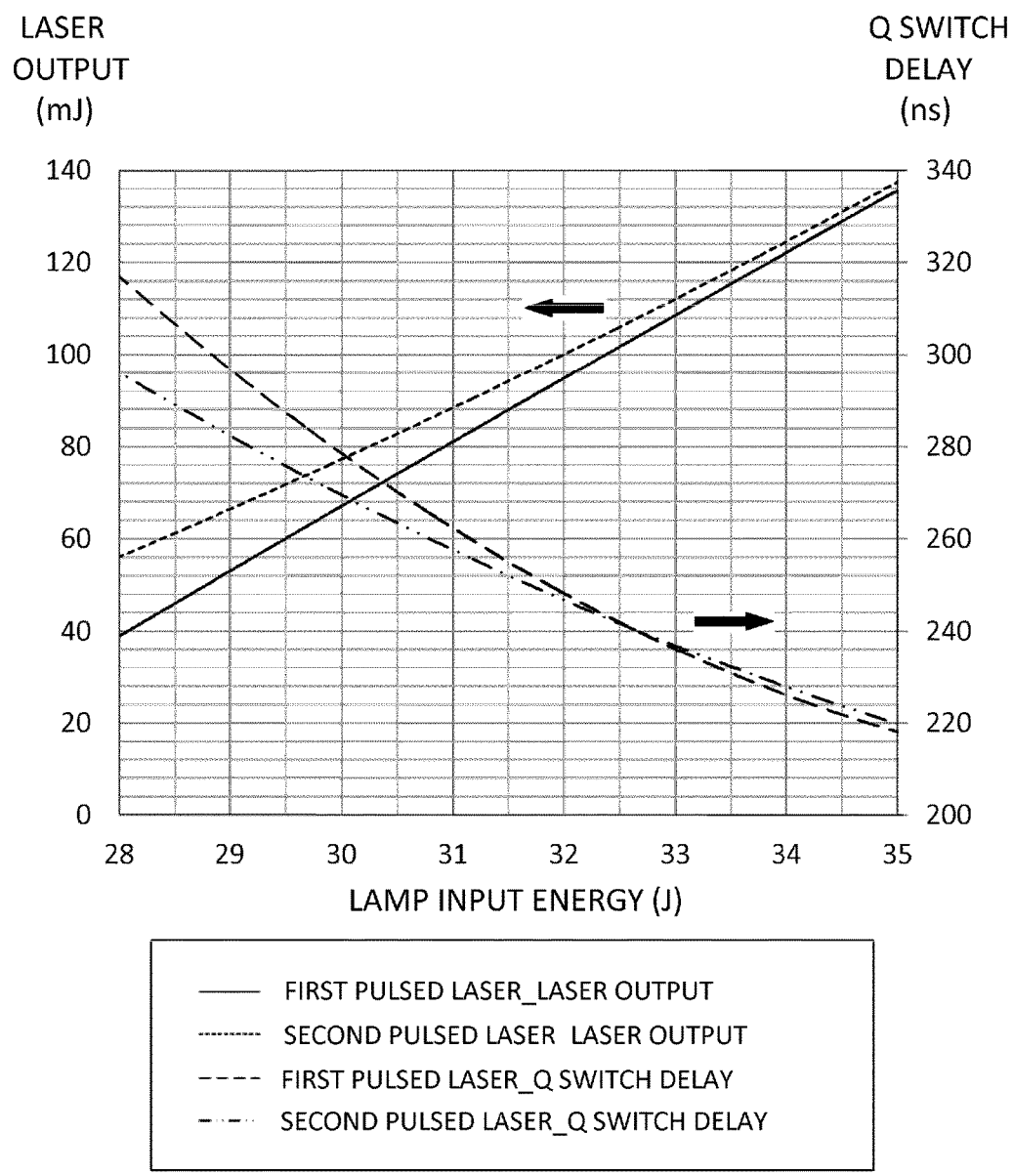
FIG. 1C is a graph depicting a relationship of input energy and laser output.

As FIG. 1C shows, if the energy to be input to the flash lamp increases, the output of the laser increases and the Q switch delay decrease. On the other hand, if the energy to be input to the flash lamp decreases, the output of the laser decreases and the Q switch delay increases. These characteristics are different between the first pulsed laser apparatus 1 and the second pulsed laser apparatus 3. These differences are caused by the individual difference between the lasers or by component breakdown over time.

For example, a case when the emission timing of the first pulsed laser apparatus 1 is earlier than the emission timing of the second pulsed laser apparatus 3, even if both pulsed laser apparatuses are controlled in exactly the same way, will be described. In this case, if the energy to be input to the flash lamp of the second pulsed laser apparatus 3 is increased, the Q switch delay of the second pulsed laser apparatus 3 decreases, and the emission timing can be closer to the first pulsed laser apparatus 1.

Conversely, if the energy to be input to the first pulsed laser apparatus 1 is decreased, the Q switch delay of the first pulsed laser apparatus 1 increases, and the emission timing of the first pulsed laser apparatus 1 delays. The emission timings of the first pulsed laser apparatus 1 and the second pulsed laser apparatus 3 can be closer by also decreasing the energy to be input to the first pulsed laser apparatus 1 and increasing the energy to be input to the second pulsed laser apparatus 3.

The energy to be input to the flash lamp can be finely adjusted, hence the emission timing of the pulsed laser can also be finely adjusted. For example, it is assumed that the initial set value of the energy to be input to the lamp is 30 J for both the first pulsed laser apparatus 1 and the second pulsed laser apparatus 3. In this case, according to FIG. 1C, the Q switch delay of the first pulsed laser apparatus 1 is 278 ns whereas the Q switch delay of the second pulsed laser apparatus 3 is 270 ns, hence the former is 8 ns later than the latter. Therefore if the energy to input to the lamp of the first pulsed laser apparatus 1 is increased to 30.5 J, then the Q switch delay becomes 270 ns for both pulsed laser apparatuses, where the emission timings match. By changing the energy to be input to the lamp, the output of the first pulsed laser apparatus 1 changes from 67 mJ to 75 mJ. The output of the second pulsed laser apparatus 3 remains 77 mJ. As a result, the pulse width of the light generated by combining the light of the first pulsed laser apparatus 1 and the light of the second pulsed laser apparatus 3 can be decreased.

By controlling the laser outputs of the pulsed laser apparatuses, that is, by controlling the energy to be input to the excitation lamps in the pulsed laser apparatuses so as to match the Q switch delays of the pulsed laser apparatuses in this way, deviation between the lights emitted from each pulsed laser apparatus can be reduced.

(Processing Flow)

Figure 1D:
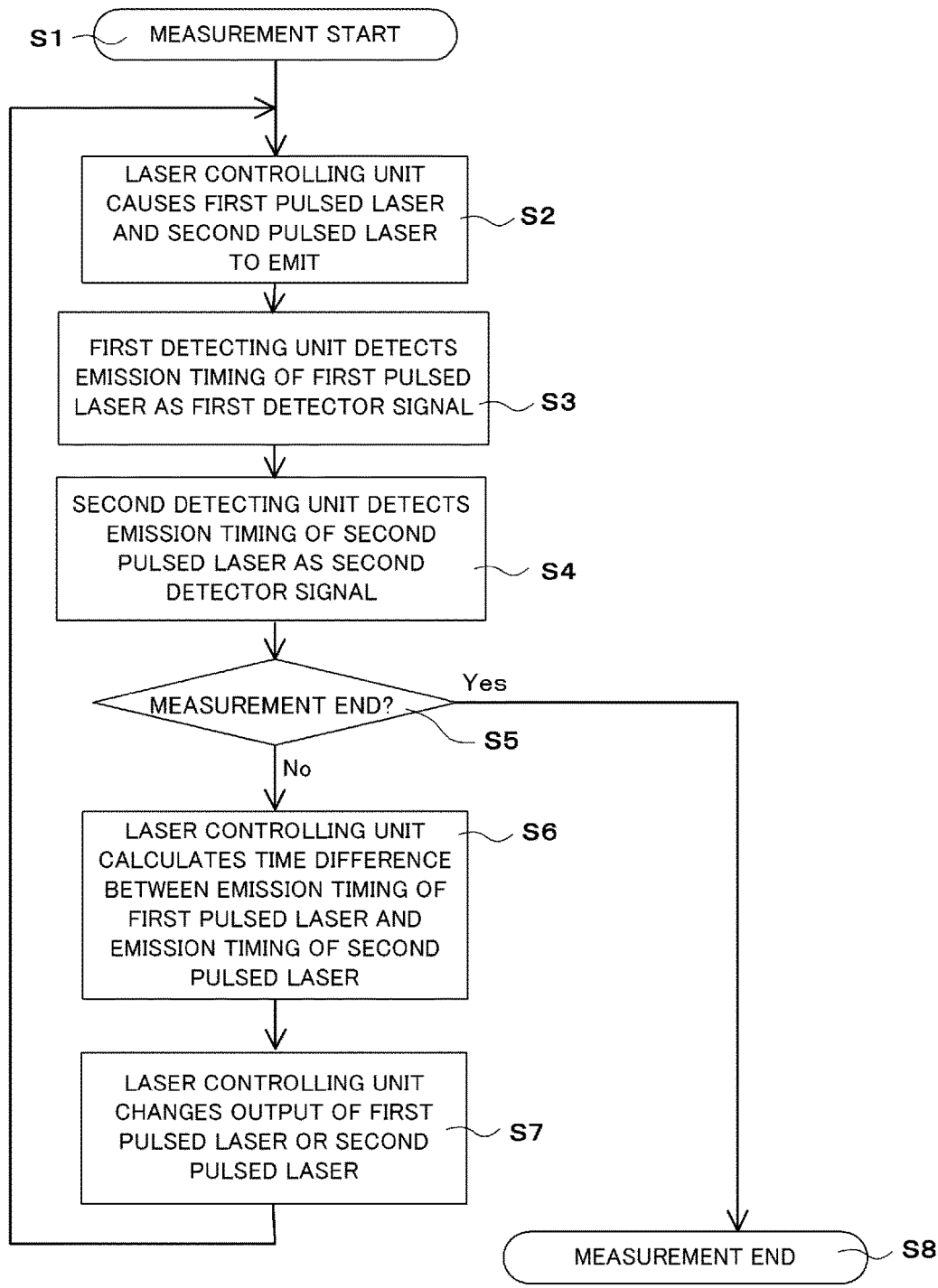
FIG. 1D is a flow chart depicting processing of Example 1.

FIG. 1D is a flow chart depicting the emission timing control of this example. First the operator starts measurement (S1). Then the laser controlling unit 9 starts emission of the first pulsed laser apparatus 1 and the second pulsed laser apparatus 3 (S2). Then the first detecting unit 6 detects the emission timing of the first pulsed laser apparatus as a first detector signal (S3). Then the second detecting unit 8 detects the emission timing of the second pulsed laser apparatus as a second detector signal (S4).

Then it is determined whether the photoacoustic measurement ended (S5). At this time, the system controlling unit (or the signal controlling unit which plays a role of the system controlling unit) determines whether the entire region of interest in the object was measured, whether a predetermined measurement count or measurement time was reached, and whether sufficient data was acquired to detect a desired SN ratio. The end of the photoacoustic measurement may be determined when the end conditions input by the user via an input device, or the end conditions stored in memory in advance, are satisfied.

If the system determines that the photoacoustic measurement ended, the measurement ends (S8). If the system determines that the photoacoustic measurement has not yet ended, on the other hand, the laser controlling unit 9 calculates the time difference between the first detector signal and the second detector signal (S6).

Then the laser controlling unit 9 changes the output of the first pulsed laser apparatus 1 or the second pulsed laser apparatus 3, so that the calculated time difference approaches 0 (S7). In concrete terms, the laser controlling unit 9 changes the energy to be input to the flash lamp of the first pulsed laser apparatus 1 or the second pulsed laser apparatus 3. In this example, the emission timing of the first pulsed laser is earlier than the emission timing of the second pulsed laser. Therefore the laser controlling unit 9 increases the energy to be input to the flash lamp of the second pulsed laser apparatus, whereby the emission timing of the second pulsed laser apparatus becomes closer to the emission timing of the first pulsed laser apparatus. Then returning to S2, the laser controlling unit 9 causes the first pulsed laser apparatus 1 and the second pulsed laser apparatus 3 to emit light again.

As described above, according to this example, the laser controlling unit controls the energy to be input to the flash lamps of the first pulsed laser apparatus and the second pulsed laser apparatus based on the time difference between the first detector signal and the second detector signal. As a result, the emission timing of the first pulsed laser and that of the second pulsed laser can be accurately matched. According to the technique disclosed in Japanese Patent Application Laid-Open No. 2011-229660, if the emission timings of the two pulsed lasers (pulse width: 13 ns) are combined at a 50 MHz clock frequency, the combined pulse width may reach 23 ns at the maximum. If the technique of this example is used, the combined pulse width can be 13 ns.

In this example, the time difference between the first detector signal and the second detector signal is adjusted to be close to 0. However the embodiments of the present invention are not limited to this. For example, if the optical path length from the first pulsed laser apparatus to the object is different from the optical path length from the second pulsed laser apparatus to the object, the arrival time of the light is longer as the optical path is longer. As a result, the arrival time of the lights to the object differs even if the lights are emitted at the same time. In such a case, to correct the difference of the optical path lengths, the time difference may be made closer to a predetermined value by increasing the energy to be input to the pulsed laser apparatus of which optical path length is longer. Further, the optical path lengths may be measured in advance and the control conditions corresponding to the measured optical path lengths may be set. This control method is effective when the difference of the optical path lengths is large, such as a case of irradiating light to both sides of the object. In other words, according to the present invention, the output of at least one of the plurality of pulsed lasers is controlled so that the time difference of the lights irradiated to the object becomes small, in concrete terms, so that the time difference of the lights irradiated to the object becomes smaller than a predetermined value.

In the example described above, the laser controlling unit controls the emission timing by controlling the energy to be input to the flash lamp. However, the embodiments of the present invention are not limited to this. The present invention can be carried out if the laser controlling unit can perform a control to influence the emission timing of the laser. In concrete terms, the laser controlling unit may control the temperature of the laser. In this case, the laser controlling unit controls the temperature of the laser medium and the resonator by a temperature controller, such as a heater or a cooler. The relationship between the laser medium temperature and the emission timing changes depending on various conditions. For example, in the case of an alexandrite laser, the emission timing advances as the temperature of the laser medium is higher. Therefore the laser medium temperature of the pulsed laser apparatus, to delay the emission timing, is decreased, or the laser medium temperature of the pulsed laser apparatus, to advance the emission timing, is increased. Since output changes if the laser medium temperature changes, controlling the laser medium temperature of the pulsed laser apparatus is the same as controlling the output of the pulsed laser apparatus.

A target of changing the energy to be input to the laser controlling unit may be one or both of the first pulsed laser apparatus and the second pulsed laser apparatus. In this example, the wavelength of the first pulsed laser apparatus and that of the second pulsed laser apparatus are the same. However, the present invention is not limited to this. For example, pulsed lasers having different wavelengths may be used. Thereby substance concentration, such as oxygen saturation in blood, can be measured. The number of pulsed laser apparatuses need not always be two, but may be three or more. This is the same for other examples described below.

Example 2

Figure 2A:
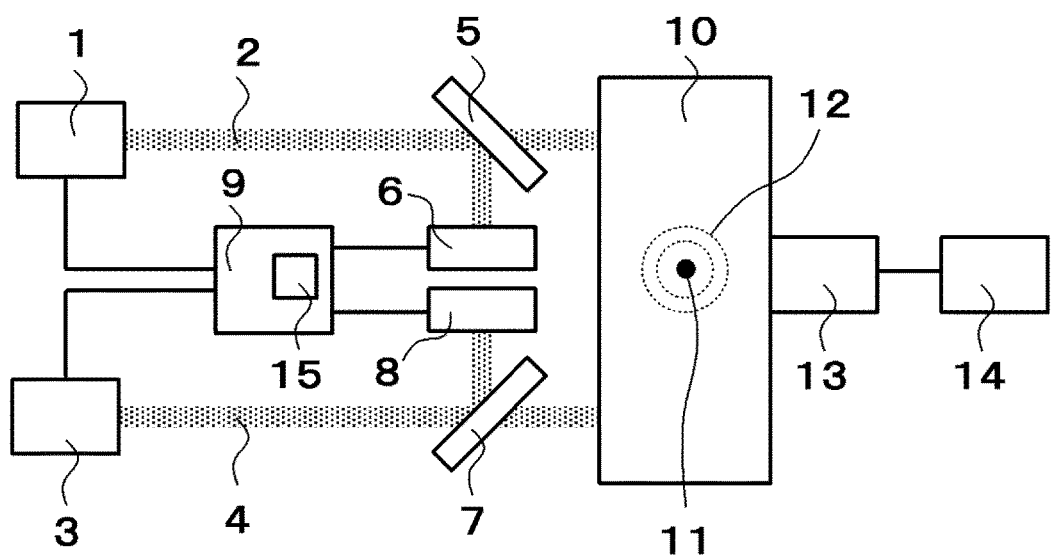
FIG. 2A is a block diagram depicting an apparatus of Example 2.

A configuration of Example 2 will be described with reference to FIG. 2A. The composing elements denoted by the reference numerals 1 to 14 are the same as FIG. 1A, therefore description thereof will be omitted.

A reference numeral 15 denotes a first storing unit. The first storing unit 15 stores an allowable time distance between the first detector signal and the second detector signal. The first storing unit 15 can be constituted by a storage device, such as a flash memory, a RAM, a magnetic disk and an HDD. The first storing unit 15 may be embedded in the laser controlling unit 9, or may be installed to be communicable with the laser controlling unit 9.

The allowable time difference may be stored in the apparatus as a fixed value when the apparatus is installed. The time the user input via an input unit (e.g. keyboard, mouse, touch panel) may be used as the allowable time difference. The allowable time difference here is a time not exceeding the clock frequency, for example. If the clock frequency is 50 MHz, the allowable time difference can be set to 20 ns or less. The allowable time distance can of course be set to be even shorter, in order to acquire a high resolution photoacoustic image.

The laser controlling unit 9 determines whether the time difference between the first detector signal and the second detector signal is longer than the allowable time difference stored in the first storing unit. If it is determined that the detected time difference is longer than the allowable time difference, the laser controlling unit 9 changes the energy to be input to the flash lamp of either the first laser controlling unit or the second laser controlling unit, so that the time difference between the first detector signal and the second detector signal becomes shorter than the allowable time difference. If the detected time difference is the allowable time difference or less, on the other hand, the laser controlling unit 9 does not change the energy to be input to the flash lamp of either the first laser controlling unit or the second laser controlling unit, but does cause the first pulsed laser and the second pulsed laser to emit light.

Figure 2B:
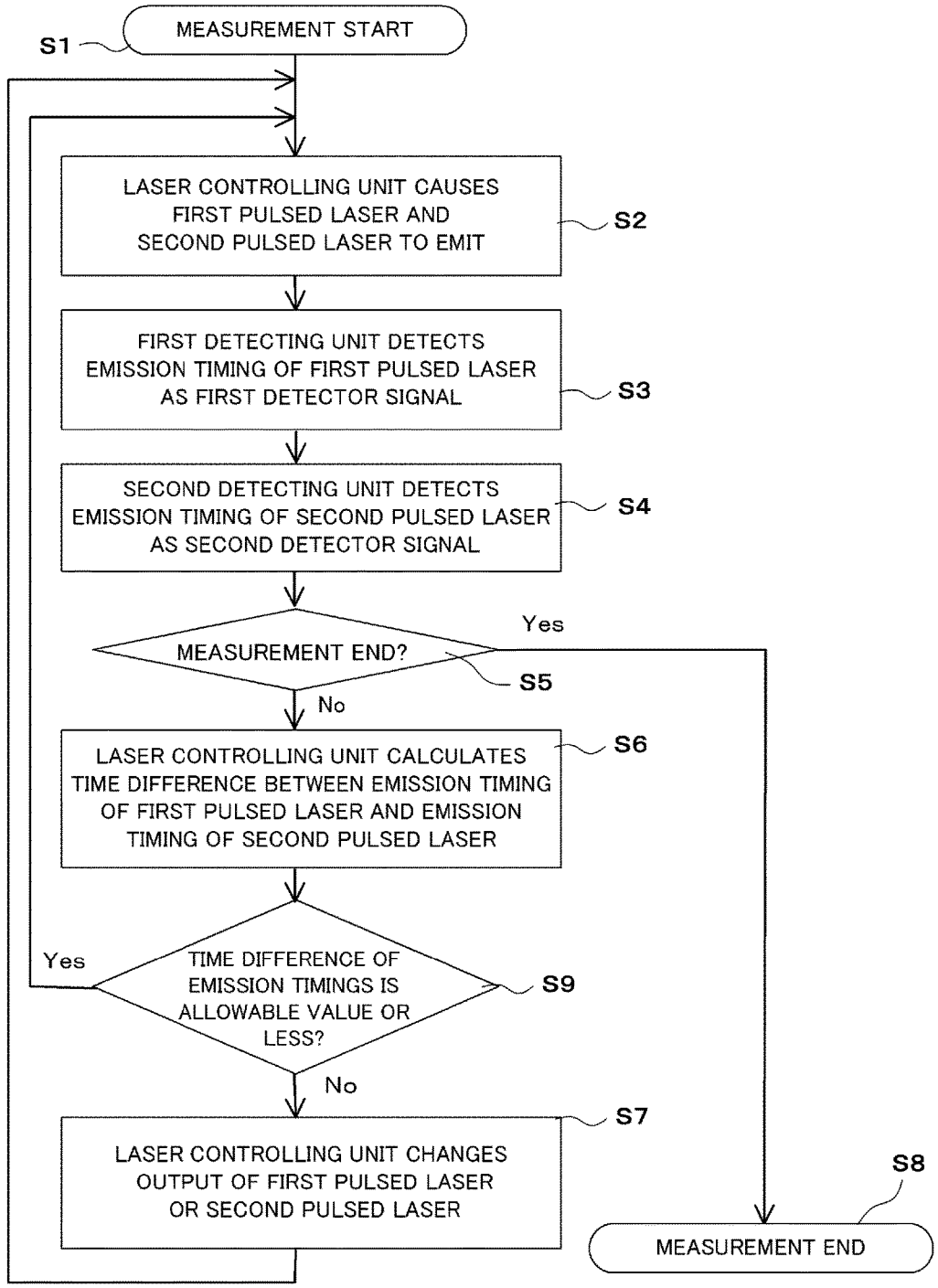
FIG. 2B is a flow chart depicting processing of Example 2.

The photoacoustic measurement flow according to this example will be described next with reference to FIG. 2B. S1 to S8 are the same as FIG. 1D, therefore description thereof will be omitted. In S9, the laser controlling unit 9 calculates the time difference between the first detector signal and the second detector signal. If the calculated time difference is the allowable time difference stored in the first storing unit or less, processing returns to S2. If the calculated time difference is longer than the allowable time difference stored in the first storing unit, processing advances to S7.

By this configuration, when the time difference between the first detector signal and the second detector signal is longer than the allowable time difference, this difference can be decreased. As a result, the pulse width, when the lights from the first pulsed laser apparatus and the second pulsed laser apparatus are combined, can be controlled to be a predetermined value or less. If the detected time difference is the allowable time difference or less, no control is needed, hence processing time can be decreased and operation load can be reduced.

Modification

Instead of the first storing unit 15 which stores the allowable time difference, the apparatus may include a third storing unit which stores the allowable value of the composite pulse width when a plurality of laser pluses are combined. The allowable value of the composite pulse width may be stored in advance as predetermined values, or may be input by the user via an input unit.

In this case, the laser controlling unit 9 controls the period when the pulses generated by the first and second pulsed laser apparatuses overlap, based on the respective pulse widths, so that a composite pulse width is within the allowable value. In concrete terms, if the composite pulse width is wider than the allowable value, the laser controlling unit delays the emission timing of one of the pulsed laser apparatuses by decreasing the input energy to the pulsed laser apparatus. If the composite pulse width in the subsequent light irradiation is within the allowable value as a result of this control, then the control conditions continue to be used. If the composite pulse width increases in the subsequent light irradiation, on the other hand, the reduced input energy is returned to the original value, and the input energy to the other pulsed laser apparatus is decreased.

Example 3

Figure 3A:
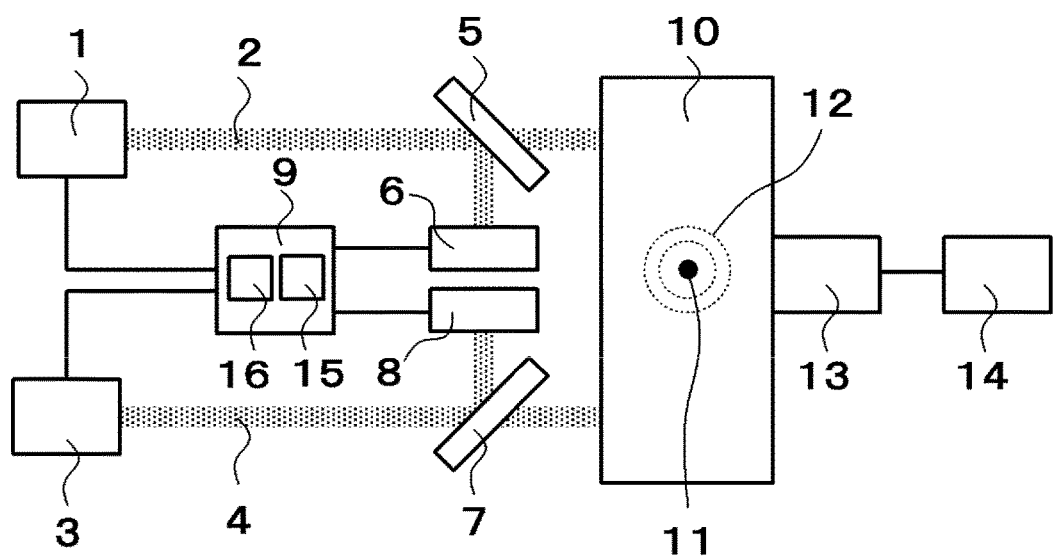
FIG. 3A is a block diagram depicting an apparatus of Example 3.

A configuration of Example 3 will be described with reference to FIG. 3A. The composing elements denoted by the reference numerals 1 to 15 are the same as FIG. 2A, therefore description thereof will be omitted.

A reference numeral 16 denotes a second storing unit. The second storing unit 16 stores a table in which a time difference between the first detector signal and the second detector signal is associated with the output conditions of the first pulsed laser apparatus and the second pulsed laser apparatus. The second storing unit 16 is constituted by a storage device similar to the first storing unit 15.

If the time difference between the first detector signal and the second detection signal is greater than the allowable time difference stored in the first storing unit, the laser controlling unit 9 refers to the table stored in the second storing unit. Then the laser controlling unit 9 changes the energy to be input to the flash lamps of the first pulsed laser apparatus and the second pulsed laser apparatus based on the output conditions acquired corresponding to the detected time difference.

Figure 3B:
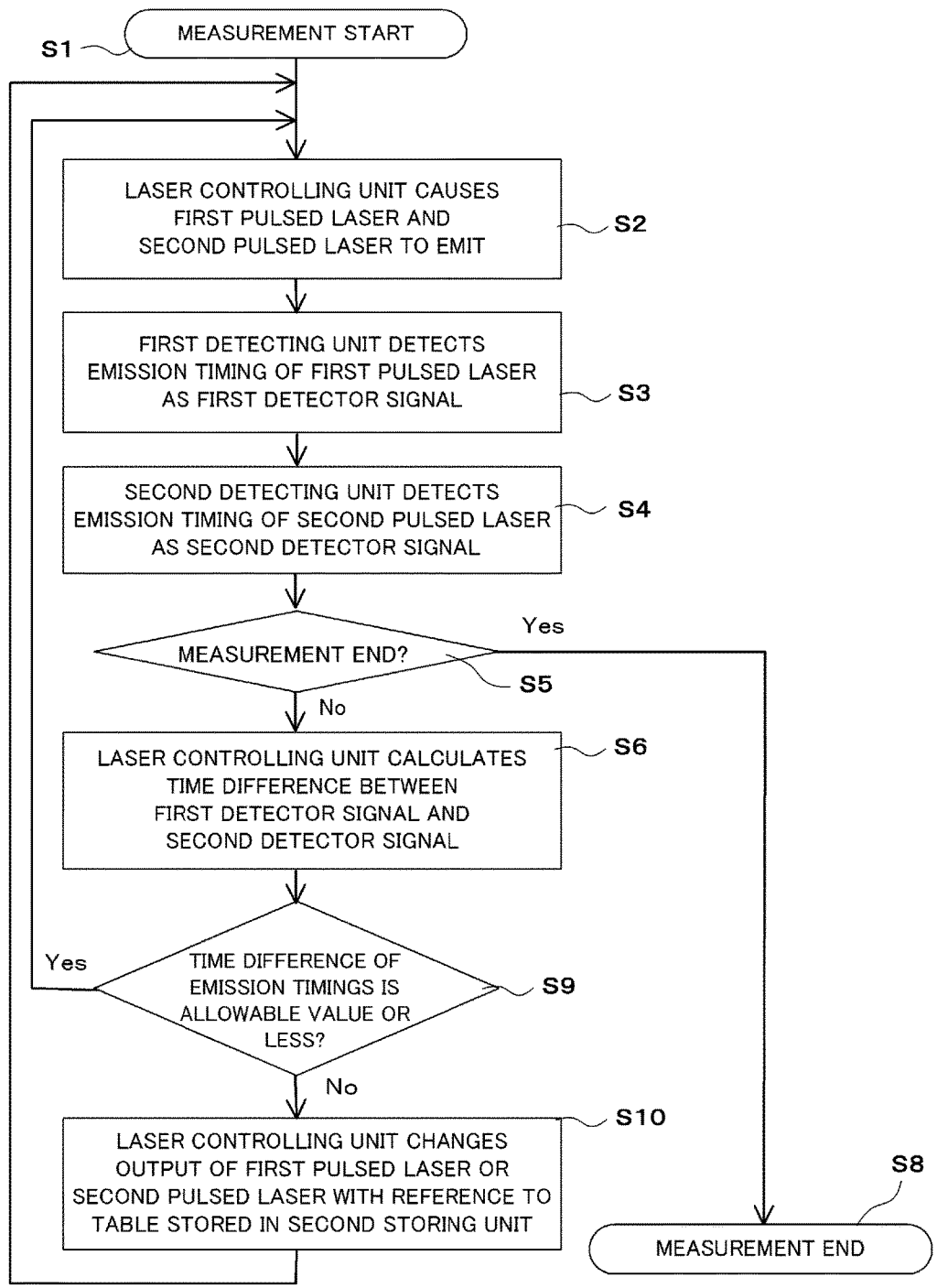
FIG. 3B is a flow chart depicting processing of Example 3.

The photoacoustic measurement flow according to this example will be described next with reference to FIG. 3B. S1 to S9 are the same as FIG. 2B, therefore description thereof will be omitted. If it is determined in S9 that the time difference between the first detector signal and the second detector signal is shorter than the allowable time difference stored in the first storing unit, processing advances to S10. Then the laser controlling unit 9 acquires the conditions on the energy to be input to the flash lamp of the first pulsed laser apparatus 1 or the second pulsed laser apparatus 3 with reference to the table stored in the second storing unit, and changes the conditions, then processing returns to S2.

By this configuration, the time difference between the first detector signal and the second detector signal can be within the allowable time difference stored in the first storing unit. As a result, the pulse width, when the lights from the first pulsed laser apparatus and the second pulsed laser apparatus are combined, can be controlled to be a predetermine value or less. In this example, the operation parameters of the pulsed laser apparatus can easily be acquired by referring to the table. The correspondence between the detector signals and the time difference may be stored in any form that can be referred to, such as a mathematical formulae, instead of a table.

Example 4

Figure 4A:
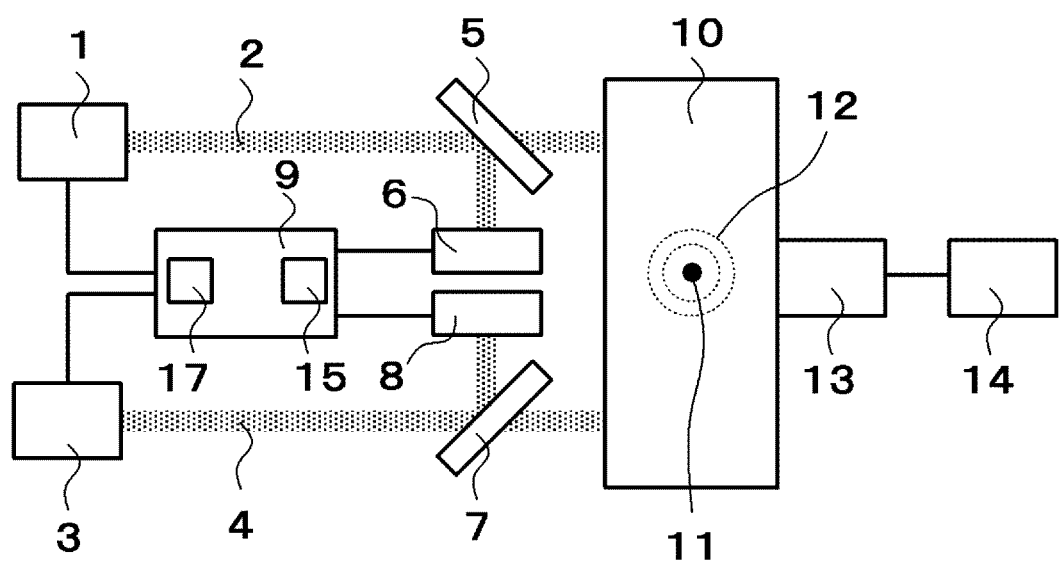
FIG. 4A is a block diagram depicting an apparatus of Example 4.

A configuration of Example 4 will be described with reference to FIG. 4A. The composing elements denoted by the reference numerals 1 to 15 are the same as FIG. 3A, therefore description thereof will be omitted.

A reference numeral 17 denotes an output limiting unit. The output limiting unit 17 has a mechanism to limit the energy to be input to the flash lamps of the first pulsed laser apparatus 1 and the second pulsed laser apparatus 3, so that the input energy does not exceed a predetermined value. The output limiting unit 17 typically is implemented by software.

Figure 4B:
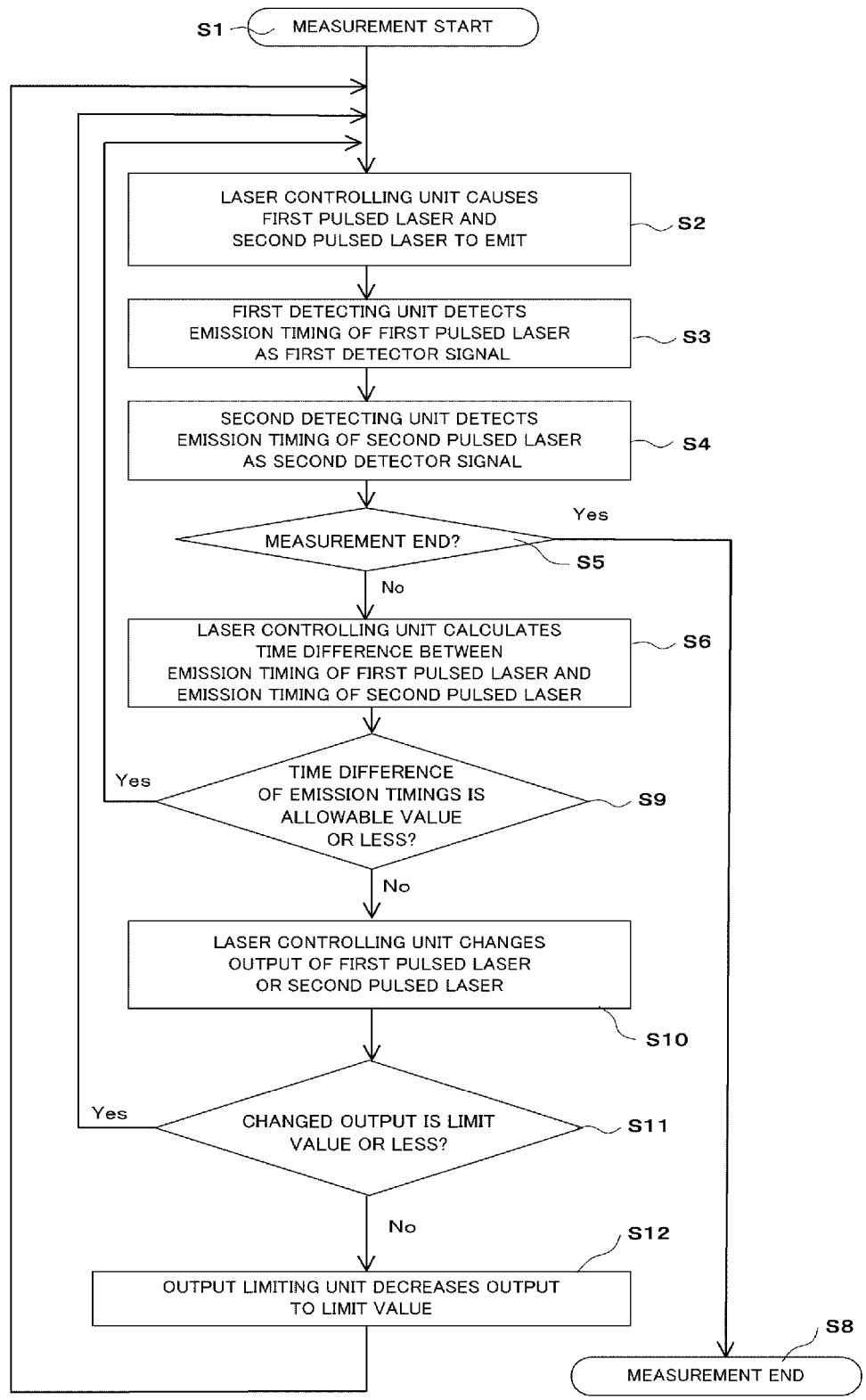
FIG. 4B is a flow chart depicting the processing of Example 4.

The photoacoustic measurement flow according to this example will be described next with reference to FIG. 4B. S1 to S10 are the same as FIG. 3B, therefore description thereof will be omitted. In S10, after the laser controlling unit 9 changes the output of the first pulsed laser apparatus or the second pulsed laser apparatus, the output limiting unit 17 determines whether the updated energy is a predetermined limit value or less (S11). If the updated output is the limit value or less, processing returns to S2. If the updated output is greater than the limit value, the output limiting unit 17 decreases the output to the limit value (S12). Then processing returns to S2.

In the case when the updated output is the limit value or more, control to decrease the energy to be input to the pulsed laser apparatus, which emits light earlier, may be performed. If this configuration is used, the outputs of the first and second pulsed laser apparatuses never rise excessively, hence the photosensitive apparatus can be more safely used.

In Example 4, an example of limiting the output using software was described, but the output may be limited using hardware as well. An example of a method using hardware is installing, as the output limiting unit, an electric circuit, which discharges an amount of energy that is stored exceeding a predetermined value, in a capacitor to store energy to be applied to a flash lamp. Hardware and software may be combined to limit output.

Example 5

Figure 5:
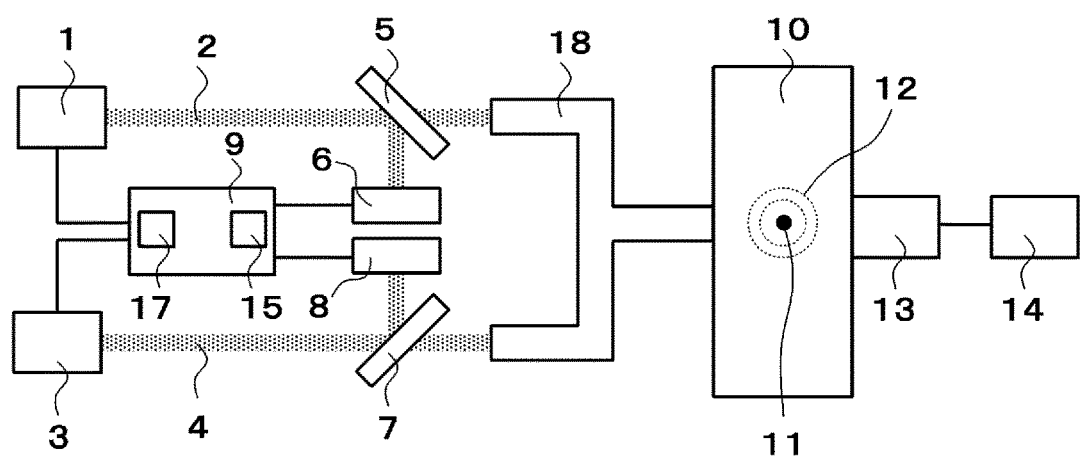
FIG. 5 is a block diagram depicting an apparatus of Example 5.

A configuration of Example 5 will be described with reference to FIG. 5. The composing elements denoted by the reference numerals 1 to 16 are the same as FIG. 4A, therefore detailed description thereof will be omitted. A reference numeral 18 denotes a light combining unit. Here a bundle fiber is used as the light combining unit 18. The light combining unit 18 has two incident ends. A light 2 emitted from the first pulsed laser apparatus 1 and a light 4 emitted from the second pulsed laser apparatus 3 enter each incident end. The lights that entered from the two incident ends are combined inside the light combining unit 18, and are emitted toward the object 10 through an emission end.

By this configuration, the depth of invasion of the light can be increased since lights irradiated to the object can be concentrated to one location. As a result, the deep area of the object can be measured well. Further, the photoacoustic signal strength can be increased, and improvement of the SN ratio can be expected.

In this example, the light combining unit has two incident ends, but the number of incident ends may be increased corresponding to the number of pulsed lasers. Further, in this example, bundle fiber is used as the light combining unit, but the present invention is not limited to this. Any means that can make the irradiation positions to the object approximately the same can be used, such as using polarization.

Example 6

Figure 6A:
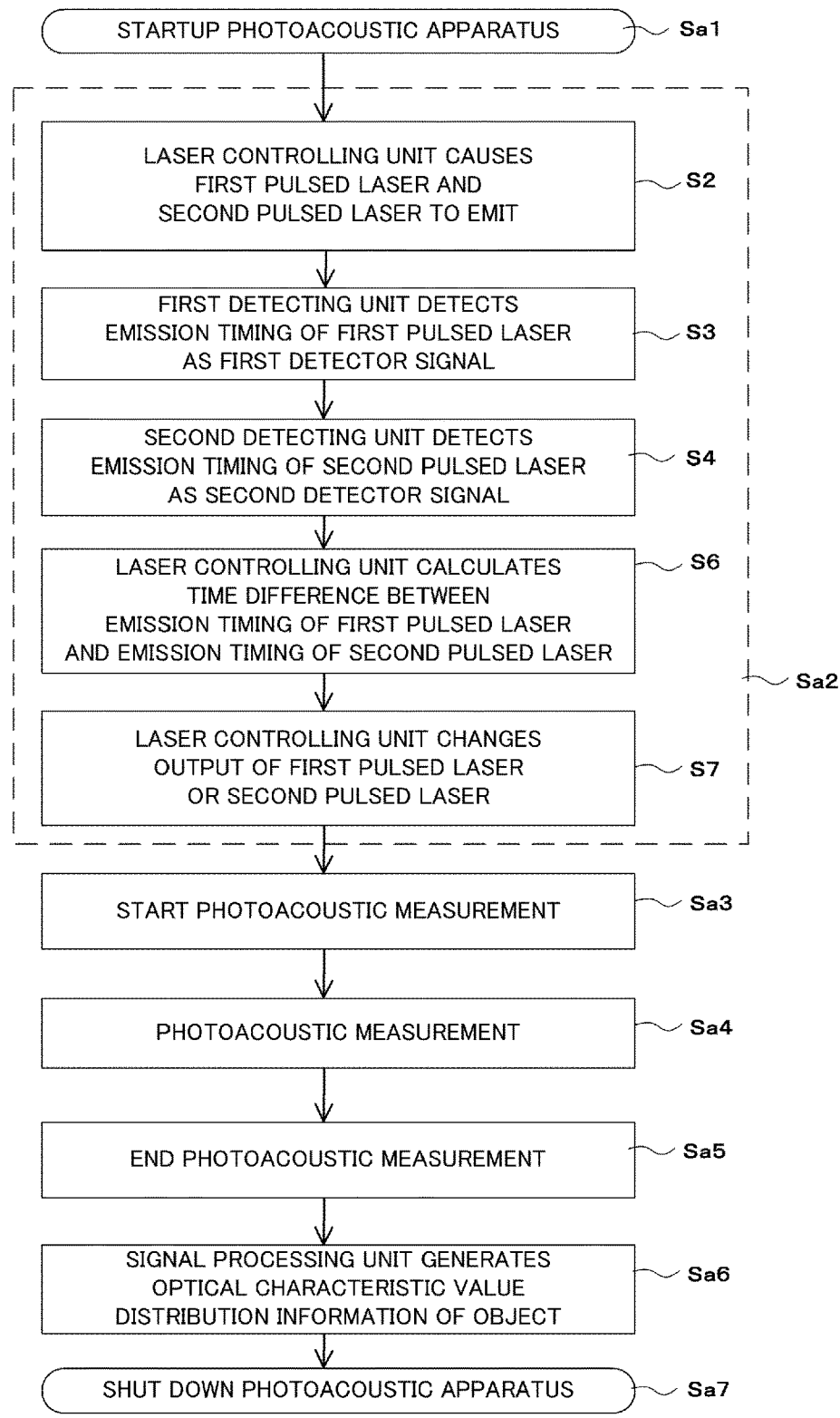
FIG. 6A is a flow chart depicting processing of Example 6.

In Example 1 to 5, the methods of controlling the emission timings of the two pulsed lasers were described. In Example 6, the timings of controlling the emission timings of the two pulsed lasers in the photoacoustic measurement will be described. The photoacoustic measurement flow according to this example will be described with reference to FIG. 6. The configuration of the apparatus of this example is the same as FIG. 1A, therefore description thereof will be omitted.

First the operator starts up the photoacoustic apparatus (Sa1). Then the apparatus automatically controls the emission timings of the first pulsed laser and the second pulsed laser (Sa2). In concrete terms, the steps in Sa2 are constituted by S2 to S4, and S6 and S7 in FIG. 1D. By the steps in Sa2, the emission timings of the first pulsed laser and the second pulsed laser match.

Then the photoacoustic measurement is started (Sa3). Next the photoacoustic measurement is executed (Sa4). Next the photoacoustic measurement ends (Sa5). Next using the photoacoustic signals acquired by the photoacoustic measurement, the signal processing unit generates the optical characteristic value distribution information of the object (Sa6). Finally the operator shuts down the photoacoustic apparatus, and the measurement flow ends (Sa7).

Figure 6B:
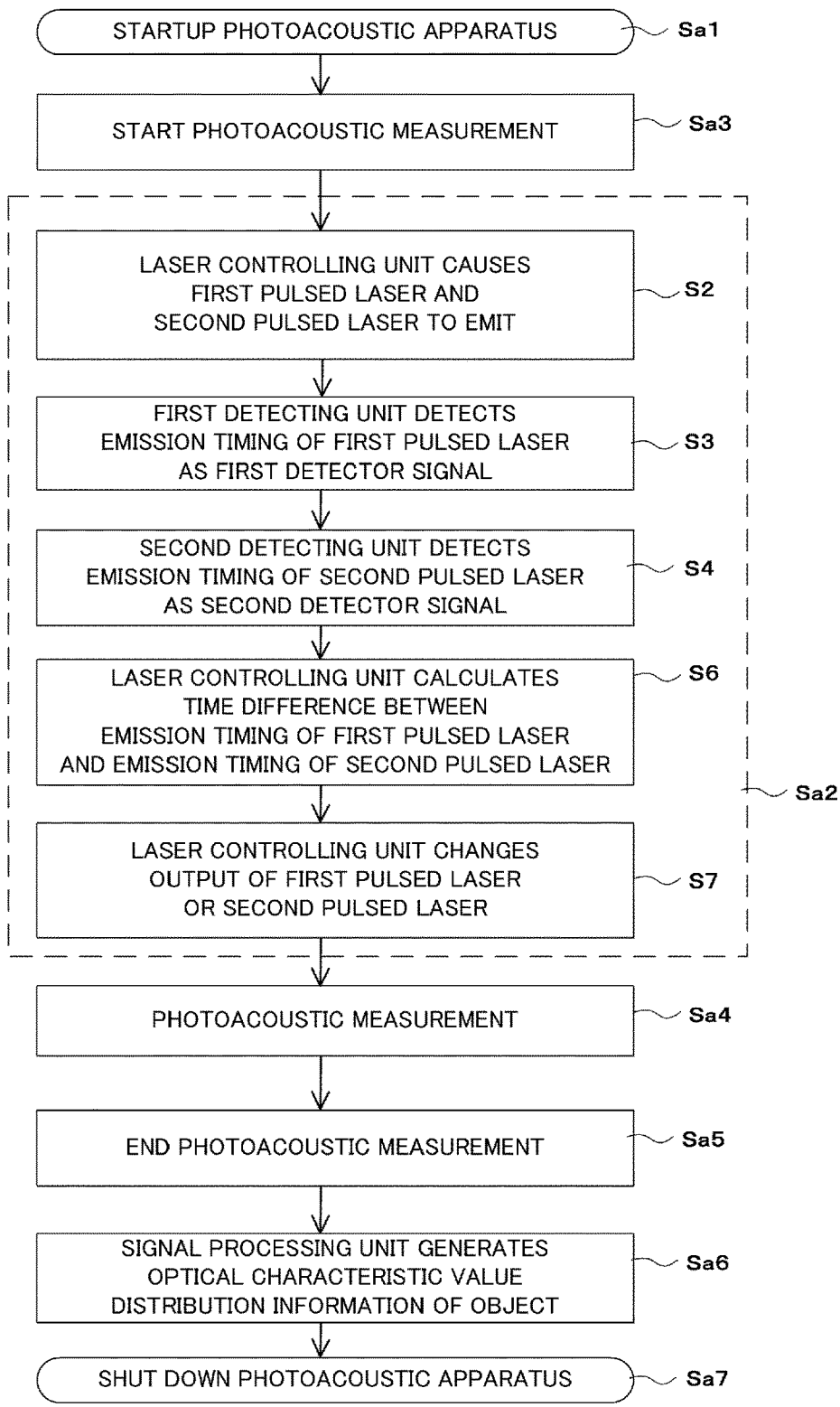
FIG. 6B is a flow chart depicting another processing of Example 6.

In this example, the control of the emission timings of the pulsed lasers is executed after starting up the photoacoustic apparatus, but the present invention is not limited to this. In concrete terms, as shown in FIG. 6B, the laser controlling unit may control the emission timings after the operator starts up the photoacoustic measurement, and the photoacoustic data may be acquired after the control. The configuration of the apparatus of this example was described using a same apparatus configuration as Example 1, but the same apparatus configuration as Example 2 to 5 may be used. In this example, the steps in Sa2 are constituted by S2 to S4 and S6 and S7 in Example 1, but may be constituted by any appropriate combination of each processing flow of Examples 2 to 5.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-131223, filed on Jun. 30, 2015, which is hereby incorporated by reference herein in its entirety.

What is claimed is:

1. An apparatus comprising:
a first laser output unit configured to output a first pulsed laser;
a second laser output unit configured to output a second pulsed laser
a laser controlling unit configured to control the first laser output unit and the second laser output unit;
a first detecting unit configured to detect an emission timing of the first pulsed laser and output a first detection signal; and
a second detecting unit configured to detect an emission timing of the second pulsed laser and output a second detection signal,
wherein the laser controlling unit controls at least one of an intensity of the first pulsed laser and an intensity of the second pulsed laser, based on a time difference between the first detection signal and the second detection signal, so as to decrease a time difference between a subsequent first pulsed laser and a subsequent second pulsed laser to be irradiated to the object.

2. The apparatus according to claim 1, wherein the laser controlling unit controls a temperature of a laser medium of the first laser output unit or the second laser output unit.

3. The apparatus according to claim 1, wherein the laser controlling unit controls the emission timings of the first and the second pulsed laser in accordance with optical path lengths from the first and the second laser output unit to the object.

4. The apparatus according to claim 1, further comprising a first storing unit configured to store an allowable time difference between the first and the second pulsed laser,
wherein the laser controlling unit controls output of at least one of the first and the second laser output unit when the time difference between the first and the second detection signal is greater than the allowable time difference.

5. The apparatus according to claim 1, further comprising a second storing unit configured to store a table in which the time difference between the first and the second detection signal is associated with control conditions for the first and the second laser outputs unit,
wherein the laser controlling unit controls output of at least one of the first and the second laser output unit with reference to the table.

6. The apparatus according to claim 1, further comprising a third storing unit configured to store an allowable value of a composite pulse width of the first and the second pulsed laser,
wherein the laser controlling unit controls output of at least one of the first and the second laser output unit so that the composite pulse width is within the allowable value.

7. The apparatus according to claim 1, wherein the laser controlling unit controls the emission timings of the first and the second pulsed laser in accordance with optical path lengths from the first and the second laser output unit to the object.

8. The apparatus according to claim 1, further comprising:
a probe configured to receive an acoustic wave generated from an object, to which the first and the second pulsed laser have been irradiated; and
a signal processing unit configured to acquire specific information on the interior of the object, based on the acoustic waves.

9. An apparatus comprising:
a first laser output unit configured to output a first pulsed laser;
a second laser output unit configured to output second pulsed laser;
a laser controlling unit configured to control the first laser output unit and the second laser output unit;
a first detecting unit configured to detect an emission timing of the first pulsed laser and output a first detection signal; and
a second detecting unit configured to detect an emission timing of the second pulsed laser and output a second detection signal,
wherein the laser controlling unit controls input energy to at least one of the first laser output unit and the second laser output unit so that at least one of an intensity of the first laser output unit and an intensity of the second laser output unit is controlled, based on a time difference between the first detection signal and the second detection signal, so as to decrease a time difference between a subsequent first pulsed laser and a subsequent second pulsed laser to be irradiated to the object.

10. The apparatus according to claim 9, wherein the laser controlling unit changes the input energy to the first and the second laser output unit so as to decrease the time difference between the subsequent first and second pulsed lasers to be output.

11. The apparatus according to claim 9, wherein the laser controlling unit increases the input energy to the laser output unit, which outputs a pulsed laser emitted at a later emission timing, out of the first and the second laser output unit.

12. The apparatus according to claim 9, wherein the laser controlling unit decreases the input energy to the laser output unit, which outputs a pulsed laser emitted at an earlier emission timing, out of the first and the second laser output unit.

13. The apparatus according to claim 9, further comprising:
a probe configured to receive an acoustic wave generated from an object, to which the first and the second pulsed laser have been irradiated; and
a signal processing unit configured to acquire specific information on the interior of the object, based on the acoustic waves.

14. An apparatus comprising:
a first laser output unit configured to output a first pulsed laser;
a second laser output unit configured to output a second pulsed laser;
a laser controlling unit configured to control the first laser output unit and the second laser output unit;
a first detecting unit configured to detect an emission timing of the first pulsed laser and output a first detection signal; and
a second detecting unit configured to detect an emission timing of the second pulsed laser and output a second detection signal,
wherein the laser controlling unit controls a temperature of a laser medium of at least one of the first pulsed laser and the second pulsed laser so that at least one of an intensity of the first laser output unit and an intensity of the second laser output unit is controlled, based on a time difference between the first detection signal and the second detection signal, so as to decrease a time difference between a subsequent first pulsed laser and a subsequent second pulsed laser to be irradiated to the object.

15. The apparatus according to claim 14, wherein the laser controlling unit changes the temperature of the laser media of the first and the second laser output unit so as to decrease the time difference between the subsequent first and second pulsed laser to be output.

16. The apparatus according to claim 14, further comprising:
a probe configured to receive an acoustic wave generated from an object, to which the first and the second pulsed laser have been irradiated; and
a signal processing unit configured to acquire specific information on the interior of the object, based on the acoustic waves.

* * * * *